United States Patent [19]
Hood et al.

[11] Patent Number: 5,370,699
[45] Date of Patent: Dec. 6, 1994

[54] MODULAR KNEE JOINT PROSTHESIS

[75] Inventors: Roger W. Hood, Olathe, Kans.; Serafin Y. Samson, Minneapolis; Robert D. Carter, Apple Valley, both of Minn.

[73] Assignee: Orthomet, Inc., Minneapolis, Minn.

[21] Appl. No.: 7,161

[22] Filed: Jan. 21, 1993

[51] Int. Cl.$^5$ .............................................. A61F 2/38
[52] U.S. Cl. ................................................ 623/20
[58] Field of Search ............................ 623/16, 18, 20

[56] References Cited

U.S. PATENT DOCUMENTS

| | | |
|---|---|---|
| 3,748,662 | 7/1973 | Helfet . |
| 3,774,244 | 11/1973 | Walker . |
| 3,816,855 | 6/1974 | Saleh . |
| 3,837,009 | 9/1974 | Walker . |
| 3,869,729 | 3/1975 | Attenborough . |
| 4,209,861 | 7/1980 | Walker et al. . |
| 4,213,209 | 7/1980 | Insall et al. . |
| 4,257,129 | 3/1981 | Volz . |
| 4,298,992 | 11/1981 | Burstein et al. . |
| 4,714,474 | 12/1987 | Brooks, Jr. et al. . |
| 4,743,261 | 5/1988 | Epinette ................................. 623/20 |
| 4,822,362 | 4/1989 | Walker et al. ......................... 623/20 |
| 4,822,366 | 4/1989 | Bolesky . |
| 4,865,607 | 9/1989 | Witzel et al. .......................... 623/20 |
| 4,936,847 | 6/1990 | Manginelli . |
| 4,936,853 | 6/1990 | Fabian et al. . |
| 4,938,769 | 7/1990 | Shaw . |
| 4,944,760 | 7/1990 | Kenna . |
| 4,950,298 | 8/1990 | Gustilo et al. . |
| 5,002,547 | 3/1991 | Poggie et al. . |
| 5,007,933 | 4/1991 | Sidebotham et al. . |
| 5,037,423 | 8/1991 | Kenna . |
| 5,047,058 | 9/1991 | Roberts et al. . |
| 5,062,852 | 11/1991 | Porr et al. ............................... 623/20 |
| 5,080,624 | 1/1992 | Jacobs et al. ........................... 623/20 |
| 5,080,675 | 1/1992 | Lawes et al. ............................ 623/20 |
| 5,108,442 | 4/1992 | Smith ....................................... 623/20 |
| 5,152,297 | 10/1992 | Luckman et al. ...................... 623/20 |

*Primary Examiner*—David Isabella
*Attorney, Agent, or Firm*—Fredrikson & Byron

[57] ABSTRACT

An implantable knee joint prosthesis which comprises a tibial tray, an articulating tibial insert attached to the tibial tray, and a femoral condylar component adapted to cooperatively bear upon the tibial insert. The femoral component has an intercondylar recess having parallel lateral side walls and posterior and anterior bearing members defining the boundaries of the recess. The tibial insert includes an eminence extending superiorly into the intercondylar recess and dimensioned and shaped to provide defined stabilization limits for preventing posterior-anterior dislocation while allowing limited translation and essentially free rotation and angulation throughout most of the total range of articulation. Metal reinforcements serve to secure the insert to the tray. Bearing surfaces of the eminence and the intercondylar recess are so shaped as to increase the area of contact between them as the degree of flexion of the leg increases to thereby limit the contact stress transmitted to the eminence and to reduce wear of the eminence.

12 Claims, 7 Drawing Sheets

MODULAR KNEE JOINT PROSTHESIS

BACKGROUND OF THE INVENTION

1. Field of the Invention

The present invention relates to implantable knee joint prostheses for replacement of the engaging surfaces of the femur and tibia of a dysfunctional human knee joint, and particularly to a modular system for allowing the physician to select and connect together appropriately sized components which provide posterior stabilization of the knee while allowing essentially free translation, rotation and angulation through the range of articulation of the knee, while still avoiding dislocation.

2. Brief Description of the Prior Art

Implantable knee prostheses for diseased and/or damaged human knees have typically employed three components, namely, the femoral, tibial and patellar replacement components. These components are surgically implanted in patients whose knee joints have deteriorated resulting from injury, arthritic disease processes or failed previous prostheses. Surgical procedures involve the trimming of the femur and tibial joint surfaces to accommodate the appropriately sized components of the prosthesis. Typically, the surgeon is required to have available a number of differently sized and configured knee joint prostheses on hand in order to make a judgment as to which prosthesis to employ in the surgical procedure with the particular patient. In the past, the components of the knee prosthesis have been factory assembled or, as described in U.S. Pat. Nos. 4,936,853 and 4,822,366, separate modular component parts of the complete knee prosthesis are maintained at hand for assembly in the operating room at the time of surgical implantation.

The selection of a particular prosthesis for a knee joint is based largely on the condition of the patient's knee and depends upon whether there is little disease or injury of the bones, ligaments and other tissues or whether there are severely damaged joints which require implantation of components that have greater inherent stability and augments for enhancing component fixation.

The knee joint prosthesis described and shown in U.S. Pat. No. 3,837,009 is exemplary of a posterior stabilized prosthesis. It includes a post that extends upwardly from the tibial component into a slot between the femoral condyles in the femoral component. An axle affixed to the femoral component and passes through an elongated hole of carefully designed shape and size in the post. Forces that are transmitted between the axle and hole can be very large, and they act at a relatively great distance from the tibial plateau; as a result, there is a fairly high degree of risk of the tibial component becoming dislodged from the tibia. A number of other known knee joint prostheses of the type that are designed to impart stability to the knee joint by mechanical action are similarly subject to failure. In some cases, the implantation of the prosthesis requires removal of a considerable amount of bone, and failure may include fracture of the remaining, weakened bone.

Between the two extremes requiring simple, small components (see, for example, U.S. Pat. No. 3,774,244) on the one hand and prostheses constructed to have inherent mechanical stability on the other is a relatively wide range of damaged knee joints in which most of the articulating surface at the joint must be replaced but most ligaments and other tissues that provide stability in the anatomical knee joint are undamaged or can be repaired so that essentially normal restraint and control of joint function are provided by remaining soft anatomical elements. Prostheses constructed for replacement of substantially all articulating surfaces of the bones at the joint are often referred to as "total" condylar joint prostheses, and a number of total knee joint prostheses of the condylar type have been proposed (see, for example, U.S. Pat. Nos. 3,748,662, 3,816,855 and 3,869,729).

Generally, a total knee joint prosthesis of the condylar replacement type includes a tibial component having a platform portion which replaces all of the superior surface of the tibial plateau and substitutes for the anatomical tibial condylar surfaces. The femoral component has laterally spaced-apart condylar portions joined by an intercondylar bridge and a patellar surface and thus affords replacement of substantially all of the surfaces of the femur that engage the tibia and patella. Whether or not the cruciate ligaments are retained in a condylar replacement prosthesis depends on the design.

The tibial component typically includes a tibial tray and stem (which may be integral or modular) for surgical attachment to the tibia and a modular articulating surface member (also referred to as a tibial insert) that is attached by a variety of mechanisms to the superior surface of the metal tibial tray. The tibial insert is constructed of a ultra high molecular weight polyethylene, a known polymer used for prosthesis bearing surfaces, and is shaped from a pair of laterally spaced concavities to receive the pair of laterally spaced-apart femoral condylar portions. The condylar portions of the femoral component are smoothly curved in the anterior-posterior direction generally to match in lateral profile the shapes of the condylar surfaces of the femur and smoothly convexly curved in all cross sections along their anterior-posterior extents.

Modular knee prostheses of this general description include both non-stabilized and posterior stabilized types. A non-stabilized modular knee prosthesis does not provide any substantial restraint against rotational and translational freedom of movement nor any mechanism to inhibit anterior-posterior dislocation on hyperextension or flexion and are exemplified by the above referenced '244 patent as well as the more recent U.S. Pat. No. 4,938,769. These total knee prostheses require only minor resection of bone for implantation, do not require severance of the posterior cruciate ligaments, and are suitable for relatively mild deterioration of the knee joint.

Posterior stabilized knee prostheses are used in posterior cruciate ligament deficient knee joints. They are characterized by an eminence extending superiorly between the parallel concavities of the tibial insert and into a recess or box-like intercondylar portion of the femoral component. The cruciate ligaments are normally severed, although the collateral ligaments and tendons remain intact.

The intercondylar recess is formed usually with parallel lateral side walls spaced-apart by anterior and posterior bridge members which may act as camming members for bearing against anterior and posterior camming surfaces of the eminence through virtually the entire range or a portion of the range of flexion to inhibit dislocation of the joint at hyper extension and flexion.

A number of posterior stabilized knee prostheses have been proposed and introduced for clinical use, including those disclosed in U.S. Pat. Nos. 4,209,861, 4,298,992, 4,213,209 and 5,007,933. The eminences and intercondylar portions disclosed in these patents have a variety of slows and dimensions to which greater or lesser degrees of restraint and freedom of relative movement are attributed. In the '861 patent, virtue is ascribed to virtually total contact of the posterior camming surface and camming member through the entire range of flexion, and the lateral side walls of the eminence and the recess are quite closely spaced to allow minimal translation or varus-valgus movement and virtually no rotational movement.

The '992 patent discloses an eminence and recess shaped to provide positive camming surface and member contact only after substantial flexure. The lateral side walls of the eminence and recess disclosed in the '992 patent appear to be parallel and closely spaced, permitting little if any lateral translation or rotation. The eminence and recess lateral side walls disclosed in the '209 patent are not parallel. The lateral walls of the eminence converge superiorly and away from the lateral side walls of the recess and also converge anteriorly.

The '209 patent shows the spaced concavities of a tibial articulating surface member being smoothly radiused with the rising side walls of the eminence to accept femoral condylar portions shaped to contact at least a portion of the side walls during articulation, rotation and translation. The degree of divergence between the side walls of the eminence and the walls of the recess superiorly limits the degree of lateral angulation and prevents extreme translation.

The '933 patent discloses an eminence and recess shaped to provide posterior camming surface and member contact from about 30° through full flexion. The lateral side walls of both the eminence and recess are relatively closely spaced and the parallel portions of both tend to converge superiorly. As in the '209 patent, at least a portion of the lateral side walls of the eminence are angled to converge anteriorly. The angulation of the '933 patent is relatively small to provide relatively limited rotation of the femoral and tibial components within a relatively limited range of flexion in comparison with the configuration disclosed in the '209 patent.

The physiology of the normal knee is such that as the leg is flexed, the net force component tending to translate the femoral condyles anteriorly of the tibial insert (referred to sometimes as a shear force) increases. As mentioned above, forward displacement of the femur is resisted, in the case of posterior stabilized knee prostheses, by contact between the respective posterior bearing surfaces of the tibial eminence and the intercondylar recess. The posterior bearing surface of the femoral component shown in the '933 patent is sharply rounded and makes essentially point or line contact with the confronting bearing surface of the tibial eminence throughout the range of flexure of the leg. In somewhat similar fashion, the area of contact between the posterior bearing surfaces of the components shown in the '992, '861 and '209 patents appears to be essentially constant throughout the range of flexure in which these surfaces are in contact.

In conjunction with posterior stabilized knee prostheses having a pronounced eminence, the forces brought to bear against the eminence requires secure attachment of the tibial insert to the tibial tray. Various attachment mechanisms of tibial insert to tibial trays have been used in the past; e.g., the matching dovetail and slot "snaplock" system of the AXIOM ™ Total Knee System or the dovetails and locking pin of the CPD (Central Post Design) tibial components, both sold by the assignee of the present invention. In the context of a posterior stabilized knee prosthesis, such locking mechanisms have been disclosed in the '209 patent and in U.S. Pat. Nos. 4,714,474 and 5,007,933.

Thus a number of posterior stabilized knee prosthesis have been proposed that provide varying degrees of restrained to unrestrained relative anteroposterior, rotational and translational movement of the femoral and tibial components. A need remains for a knee joint prosthesis that provides appropriate roll back and a high degree of rotation and angulation to mimic the freedom of movement of the normal knee while advantageously limiting anteroposterior dislocation (subluxation).

SUMMARY OF THE INVENTION

There is provided, in accordance with the present invention, a total knee joint prosthesis of the condylar type which is constructed to provide essentially free translation, rotation and angulation throughout most of the total range of articulation and to provide restraint and control at and near full extension and at the high end of the range of flexion, and having securely attached components.

More particularly, a knee joint prosthesis, according to the present invention, comprises a femoral component which includes a pair of laterally spaced-apart condylar portions having external surfaces that are smoothly curved in the anteroposterior direction generally to match in lateral profile the shapes of the condylar surfaces of the femur and smoothly convexly curved in all cross sections along their anteroposterior extents. The condylar portions are interconnected by a box-like intercondylar portion which defines a recess that opens toward the tibial plateau and has spaced-apart lateral side walls, an anterior bearing surface and a posterior cam bearing surface.

The tibial component of the prosthesis includes a tibial platform portion which may be made of ultra high molecular weight polyethylene and having on its relatively flat superior surface a pair of laterally spaced-apart concavities, each of which is shaped and dimensioned to receive and support in nested relation a respective condylar portion of the femoral component in all normal angulations of the knee. A central eminence extends upwardly from the relatively flat superior surface of the tibial component between the concavities and into the intercondylar recess of the femoral component.

The lateral side walls of the tibial eminence have anteriorly extending and posteriorly extending surfaces and also angled surfaces in planes that converge anteriorly from the parallel surfaces, the posteriorly extending surfaces being essentially parallel to the respective lateral side walls of the recess and the anteriorly extending surfaces being angled with respect to antero-posterior planes. The width of the eminence is selected with respect to the distance between the parallel side walls of the recess such that no contact occurs in normal articulation and a relatively high degree of varus/valgus angulation, translation and/or rotation of the tibial and femoral components must take place before any contact occurs. The freedom of movement thus provided is such that the condylar portions must be displaced laterally and out of the concavities before contact between the confronting side walls of the tibial eminence and the recess is made.

For the purpose of controlling the stress (force per unit area) that is transmitted anteriorly against the posterior bearing surface of the tibial eminence by the opposing bearing surface of the recess, the respective bearing surfaces are so shaped as to increase their area of contact as the degree of flexion of the knee increases.

These and other features of the invention are realized in a knee joint prosthesis comprising: a femoral component adapted to be implanted on the condylar portion of the femur and having a pair of laterally spaced-apart condylar portions, each of which has an external surface that is smoothly convexly curved in the anteroposterior direction and generally matches the shapes in lateral profile of the condylar surfaces of the femur and that is smoothly convexly curved in all cross sections along its antero-posterior extent. A box-like intercondylar portion interconnects the condylar portions and defines an intercondylar recess having lateral side walls spaced-apart a certain distance, an anterior stop surface and a posterior beating surface serving as a camming member. A tibial component is adapted to be implanted on the tibial plateau and includes a plate-like platform portion having on its superior surface a pair of laterally spaced-apart concavities to receive in nested relation the condylar portions of the femoral component. A central eminence extends superiorly from the platform portion and is adapted to be received in the intercondylar recess of the femoral component. The eminence has lateral surfaces, an anterior surface and a posterior surface. The relative positions and shapes of the anterior and posterior surfaces of the eminence and recess of the prosthesis, as implanted in the knee joint, permit substantially free relative antero-posterior translation of the components while restraining excessive anterior and posterior movements. The lateral surfaces of the eminence includes posterior portions essentially parallel to the lateral side walls of the recess to define a width of the eminence substantially narrower than the distance between the spaced-apart lateral side walls, and anterior portions angled with respect to anterior-posterior planes for enabling medial/lateral translation and substantial varus/valgus angulation and relative rotation between the tibial component and the femoral component within a substantial portion of the range of flexion. The respective posterior bearing surfaces of the tibial eminence and of the intercondylar recess are so shaped as to increase their area of contact as the degree of flexion of the leg increases.

Thus in accordance with the present invention a high degree of freedom in rotation, angulation and translation is involved in the fashion of a non-stabilized knee prosthesis while the posterior and anterior camming surfaces and members of the eminence and recess, respectively, provide anteroposterior stability with reduced stress against the tibial eminence.

The advantages of the joint of the present invention are kinematic in nature. The narrow eminence and limited range of contact provide posterior rollback and prevent posterior tibial dislocation, thus mimicking the normal action of the posterior cruciate ligament. The collateral ligaments and remaining soft tissue structures provide the constraint in rotation and angulation within the wide range allowed by the prosthesis and absorb loads that otherwise would lead to wear or loosening of the femoral and/or tibial components.

The knee joint prosthesis of the present invention is further characterized by a secure attachment of the tibial insert to the tibial tray that bears the loads placed on the eminence when it is contacted by the side walls and/or the anterior stop surface or posterior camming member.

The tibial insert, fabricated of low friction, ultra high molecular weight polyethylene, has metal inserts fitted in it to reinforce its attachment upon the superior surface of the tibial tray. The attachment is accomplished by a pair of dovetail-shaped grooves in the inferior surface of the tibial insert shaped to receive a like pair of dovetail-shaped bosses on the superior surface of the tibial tray. A recess in the superior surface of the tray extends perpendicularly to the bosses and receives a metal pin reinforced bars extending inferiorly from the tibial insert to lock it in place. The dovetail-shaped grooves of the insert are reinforced with a metal insert to enhance the strength of attachment to the tray.

BRIEF DESCRIPTION OF THE DRAWINGS

The features of the present invention can be best understood, together with further objects and advantages thereof, by reference to the following description taken together with the appended drawings in which like reference numbers refer to like parts, and which describe some embodiments of the present invention.

DETAILED DESCRIPTION OF THE PREFERRED EMBODIMENTS

Figure 1:
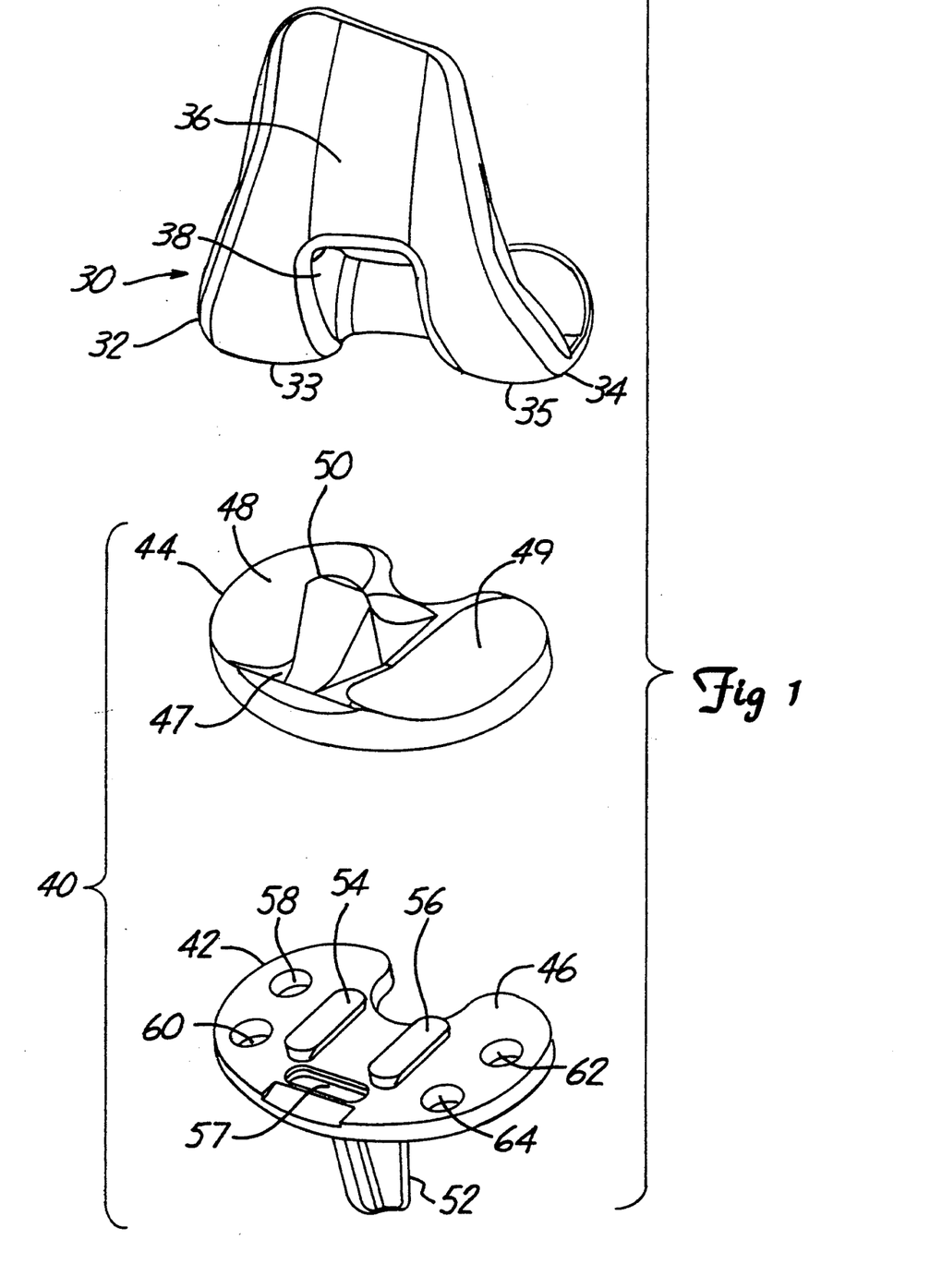
FIG. 1 is an exploded perspective view of the assembly of one embodiment of the knee joint prosthesis of the present invention.
Figure 2:
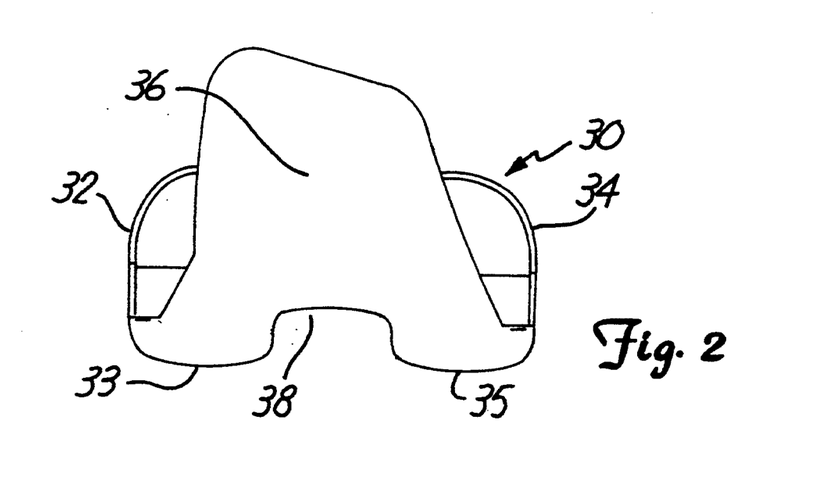
FIG. 2 is an anterior elevation view of the femoral component of the knee joint prosthesis of FIG. 1.
Figure 3:
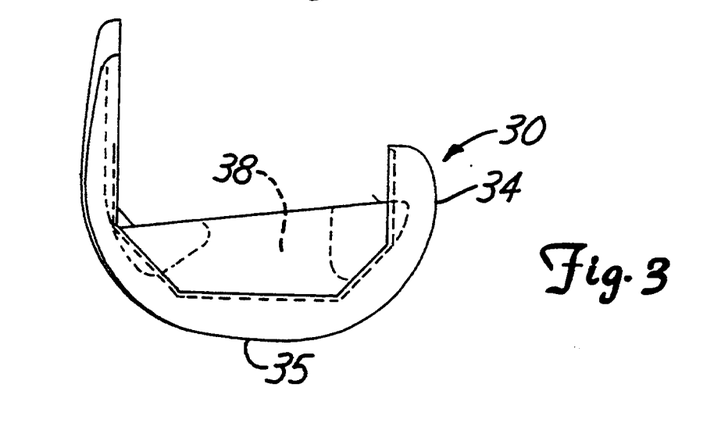
FIG. 3 is a side elevation view of the femoral component.
Figure 4:
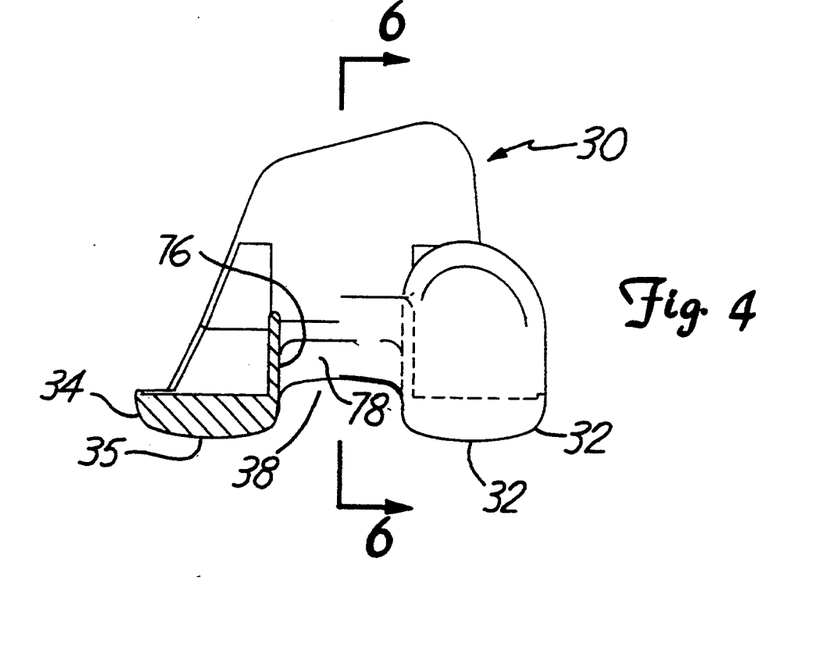
FIG. 4 is a posterior elevation view of a femoral component in partial cross sections.
Figure 5:
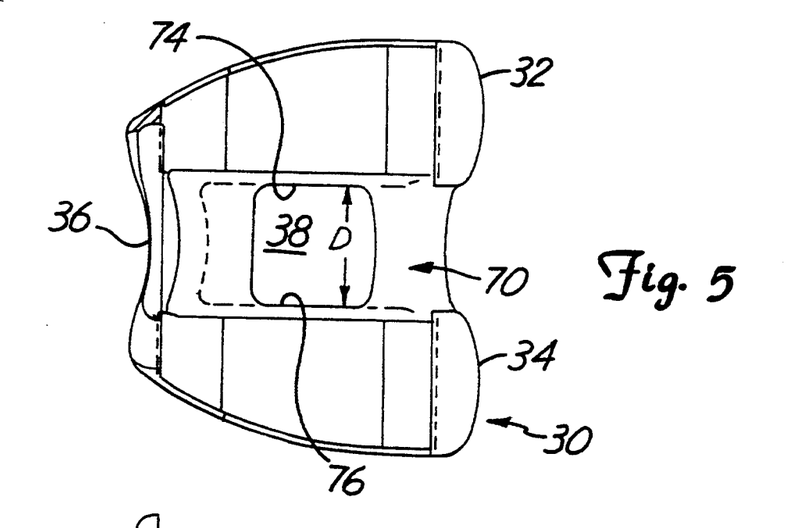
FIG. 5 is a top view of the femoral component.
Figure 6:
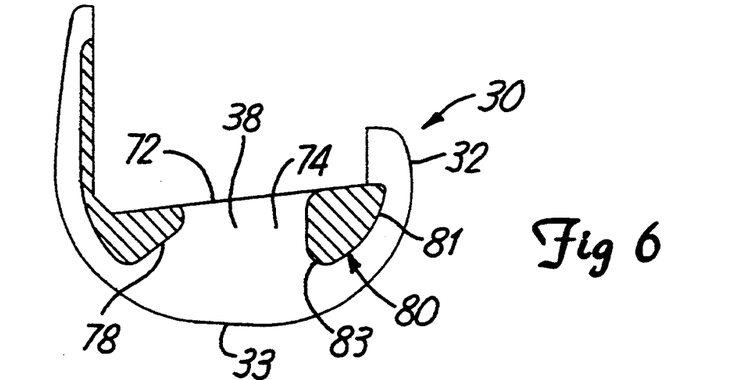
FIG. 6 is a side cross section view along section lines 6—6 of FIG. 4.

Referring now to the drawings, and especially to FIG. 1 thereof, a knee joint prosthesis constructed in accordance with one embodiment of the invention is illustrated in exploded view. The prosthesis includes the femoral component 30 and tibial component 40 comprising a tibial tray 42 and tibial insert 44. If desired, the tibial component 40 may be provided as an integral component fabricated, for example, from ultra high molecular weight polyethylene. In the depicted embodiment, the tibial insert 44 is fitted onto the proximal surface 46 of the tray 42 in a manner to be described.

The femoral component 30 includes the two condyles 32 and 34, a patellar groove 36 and an intercondylar recess 38 described in greater detail hereafter in conjunction with FIGS. 2-6.

The tibial insert 44 has a pair of concavities 48, 49 carved into the generally flat surface 47 for receiving the bearing surfaces of the condyles 32 and 34. Arising centrally from the insert is a superiorly projecting eminence 50 adapted to fit within the recess 38 of the femoral component 30 in a manner to be described hereafter.

The tibial tray 42 includes an inferiorly extending tibial stem 52 to be received in the cavity created surgically in the tibia for stabilizing its attachment thereto. A pair of longitudinally extending raised dovetails 54 and 56 extend above the surface 46 of the tray 42 and match cutout grooves in the distal or inferior surface of the insert 44 in a manner to be described hereafter. Four holes 58, 60, 62, 64 are provided through the surface 46 of the tibial tray 42 to receive tibial elements positioned against the inferior surface 66 where necessary to achieve proper contact with the remaining tibial bone.

FIGS. 2-6 depict in greater detail the design and features of the femoral component 30. The femoral component 30 is constructed in one piece, preferably of a biocompatible high-strength alloy, such as a cobalt-chrome alloy, that includes the two condylar components 32 and 34 each having an inferior, convexly shaped articular surface 33 and 35, respectively, which bear against the concavities 48, 49, respectively, of the tibial insert 44. The condylar portions 32, 34 are joined together by the patella region 36 depicted in FIG. 2 and the box-like bridging portion 70 depicted in the other figures. The box-like portion 70 defines the intercondylar recess 38 and includes parallel side walls 74 and 76 spaced-apart a distance D. The intercondylar recess may simply be open at its top, as shown at 72 in FIG. 6, or may be supplied with a superior wall or roof. A sloping surface 78 extending generally inferiorly and anteriorly defines the anterior stop surface at one end wall of the recess 38. The posterior end wall of the recess 38 is defined by the camming bearing member 80, the bearing surface of which continuously varies from a gently rounded posterior section 81 to a somewhat more severely rounded anterior section 83. As shown best in FIG. 6, surface section 81 is formed on a radius that is much greater (at least twice as great) as that of the more severely rounded surface section 83.

Figure 7:
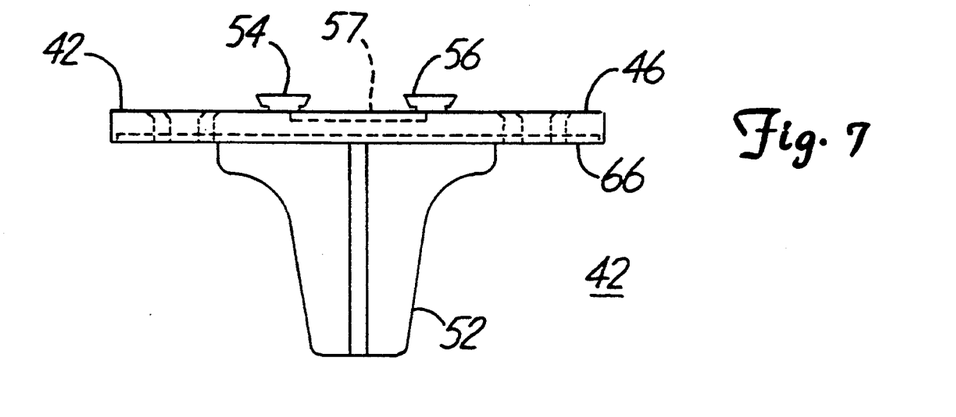
FIG. 7 is an anterior elevation view of the tibial tray component of the knee joint prosthesis of FIG. 1.
Figure 8:
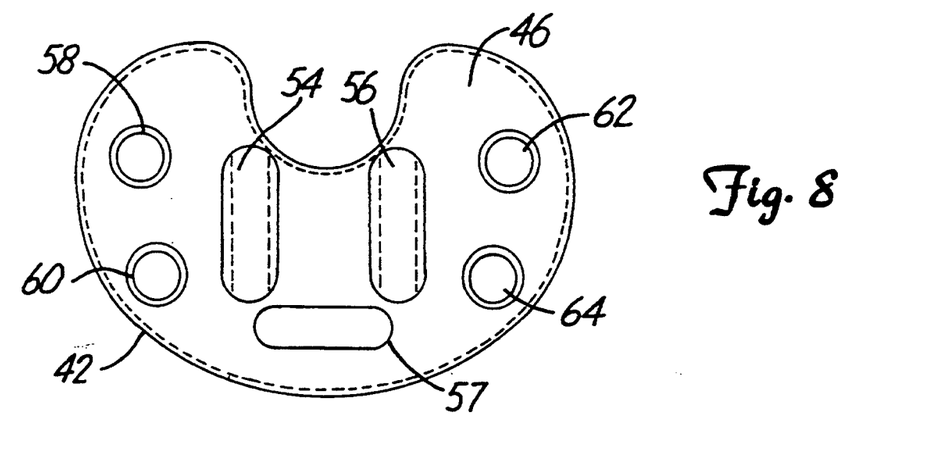
FIG. 8 is a top view of the tibial tray component.
Figure 9:
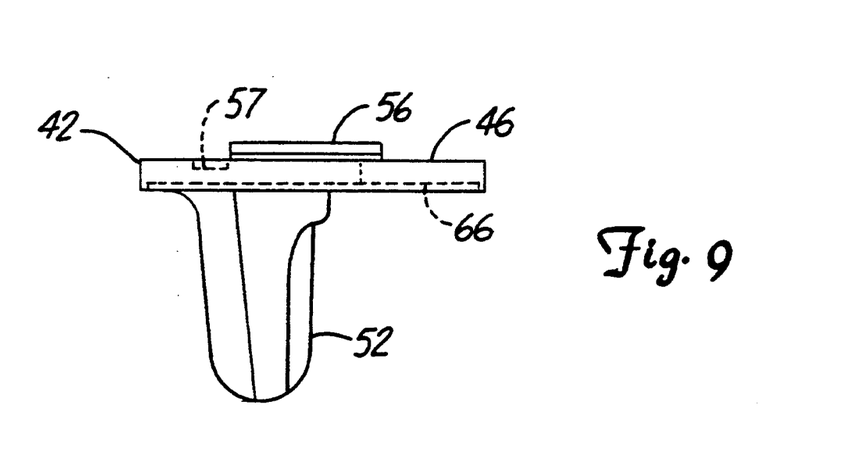
FIG. 9 is a side elevation view of the tibial tray component.

FIGS. 7-9 illustrate the tibial tray 42 in top and elevation views. A pair of elongated, dovetail-shaped bosses 54, 56 extend superiorly from the surface 46 of the tray 42 and parallel to one another. An elongated recess 57 is cut into the surface 46 perpendicular to the direction of the bosses 54, 56. The tibial tray 42 corresponds to the prior art AXIOM TM tibial tray sold by the assignee of the present invention, wherein the bosses 54, 56 and recess 57 act to retain a tibial insert 44 which has matching dovetail shaped grooves cut in its inferior surface and a boss 51 projecting from that surface that engages in the slot 57 when the dovetail bosses 54 and 56 are fully inserted into the matching grooves 53, 55. The through-holes 58, 60, 62, 64 each receive a cancellous screw in holes drilled into the tibia to aid in fixation of the tibial component.

Figure 10:
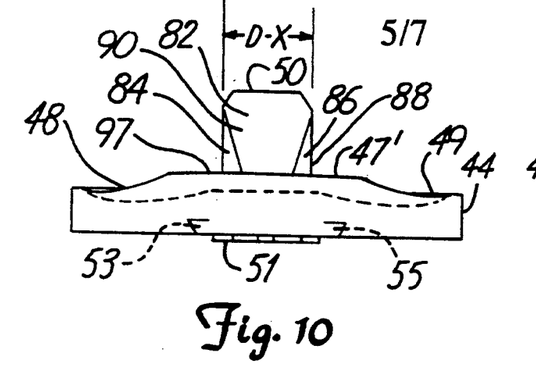
FIG. 10 is an anterior elevation view of the first embodiment of a tibial insert of the knee joint prosthesis of FIG. 1.
Figure 11:
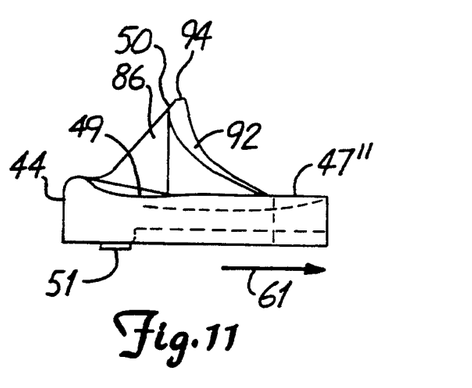
FIG. 11 is a side elevation view of the tibial insert of FIG. 10.
Figure 12:
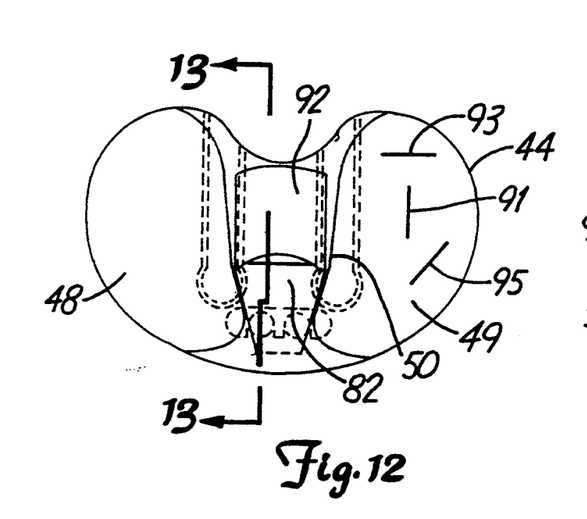
FIG. 12 is a top view of the tibial insert of FIG. 10.

The grooves and bosses are shown more clearly in FIGS. 10 to 12 which illustrate a first embodiment of the tibial insert 44 of the present invention. In FIG. 10, an elevation view of the tibial insert 44 depicts an anterior view of the stop member 51 which snaps into the groove 57 and the elongated dovetail-shaped cutout grooves 53 and 55 that engage with the dovetail-shaped bosses 54 and 56, respectively. To attach the tibial insert 44 to the tibial tray 42, the grooves 53 and 55 are lined up with the dovetail-shaped bosses 54 and 56 and advanced in the direction of the arrow 61 depicted in FIG. 11 until the projection 51 snaps into the groove 57.

Turning now to the shape and construction of the eminence 50 and the concavities 48, 49, it should first be noted that the concavities 48, 49 are cut into the upper surface 47 of the tibial insert 44. The upper surface 47 has an upper level 47' connected with the lower level 47" alongside the eminence 50.

In FIG. 10, the eminence 50 is shown having parallel side walls of a width equal to D-X, that is, narrower by a distance X than the distance D between the lateral side walls 74 and 76 of the recess 38 depicted in FIGS. 2-6. FIG. 10 also shows the stop surface 82 sloping anteriorly and adapted to engage the sloping surface 78 of the bridging portion 70 depicted in FIGS. 3 and 6 upon hyper-extension of the knee joint prosthesis. The surface 82 is bounded by the anteriorly convergent planar side wall surfaces 84 and 86 which are oriented at an angle of about 15° to the posterior parallel side walls 88 and 90. The posteriorly descending cam or bearing surface 92 has a slight convex curvature in a lateral direction and has a gentle concave curvature in the antero-posterior direction to act as a cam follower for the cam lobe bearing member 80 of the bridging portion 70 depicted in FIGS. 3 and 6, the latter curvature being such as to match the antero-posterior curvature of the gently rounded surface 80.1 of the posterior bearing surface of the femoral component. A flattened peak 94 caps the eminence 50 so that it fits generally within the opening 72 of the box 70.

Figure 17:
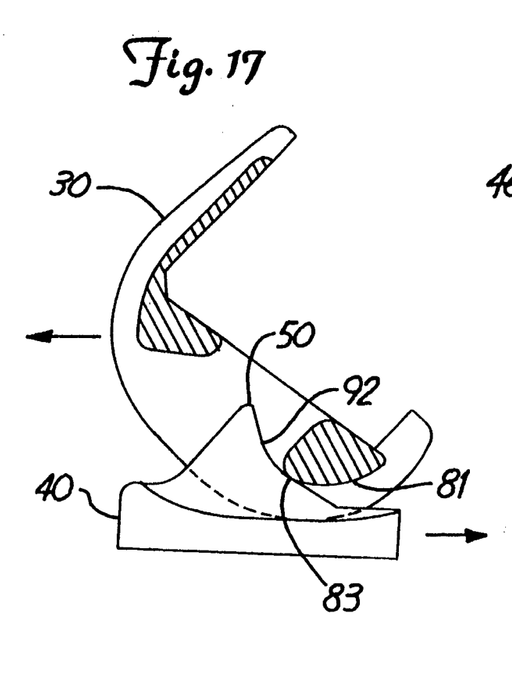
FIG. 17 is a schematic view of the prosthesis of FIGS. 16A–16F showing restraint of anterior movement of the femur.

In operation, the articulating surfaces 33 and 35 bear against the dished-out concavities 48 and 49 and allow the knee joint to articulate between a hyper-extended and a fully flexed position. Normally there is no contact in the range of normal articulation or leg angulation from full extension to about 65°-70° (preferably 69°) of flexion. However, if subluxation of the femoral component with respect to the tibial component occurs, as shown in FIG. 17, contact between the bearing surfaces 83 and 92 of the respective femoral and tibial components restrains dislocation of the knee.

As normal flexion continues beyond e.g., 69°, the posterior cam bearing surface 83 contacts and bears against the posterior camming surface 92 and gradually rides up that surface as the degree of flexion increases through the remaining range to the fully flexed position. The relative positions of the respective posterior bearing surfaces is illustrated in FIGS. 16A-16F. As flexion continues beyond about 69°, the amount of contact between the respective bearing surfaces increases. In FIG. 16 D, for example, the area of contact between the posterior bearing surfaces is rather small as contact first occurs at 69°, whereas in FIG. 16 F, the contact area has substantially increased. Whereas the posterior bearing surface 83 of the femoral component is of metal, the opposing posterior bearing surface 92 of the tibial eminence is of polyethylene and is much softer and subject to damage. By increasing the area of contact between these surfaces, the anteriorly directed shear force is spread over a larger area as this force increases with increasing knee flexion, thereby reducing the stress (in terms of force per unit area) to which the surface 92 would otherwise be subjected.

In accordance with the present invention, the width D-X (FIG. 10) is selected in relation to the distance D (FIG. 5) so as to provide for relatively free rotation, varus/valgus angulation and translation of the joint through the entire range of flexion. The degree of rotation is enhanced by the substantial 15° orientation of the lateral surfaces 84 and 86 to the parallel side walls 88 and 90.

In FIG. 12, the arrows 91 depict the direction of movement of the articulating surfaces 33 and 35 during normal articulation and arrows 93 and 95 depict the direction of medial/lateral translation and rotation effected by the difference X and the 15° angle. The actual degree of rotation may be greater than 15° in either direction due to the play introduced by the difference X.

The tibial insert 44 is preferably formed of a suitable biocompatible bearing material, such as ultra high molecular weight polyethylene, and preferably is constructed in one piece with the eminence 50. The forces that are brought to bear against the eminence 50 could cause the attachment mechanism of the tibial insert 44 with the tibial tray 42 as described above to fail. Consequently, the tibial insert is reinforced in the preferred embodiments illustrated in FIGS. 12-14.

Figure 13:
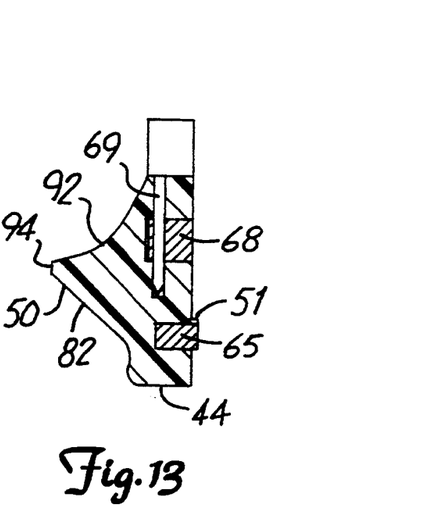
FIG. 13 is a cross-section view of the tibial insert of FIG. 12 taken along lines 13—13 of FIG. 12.
Figure 14:
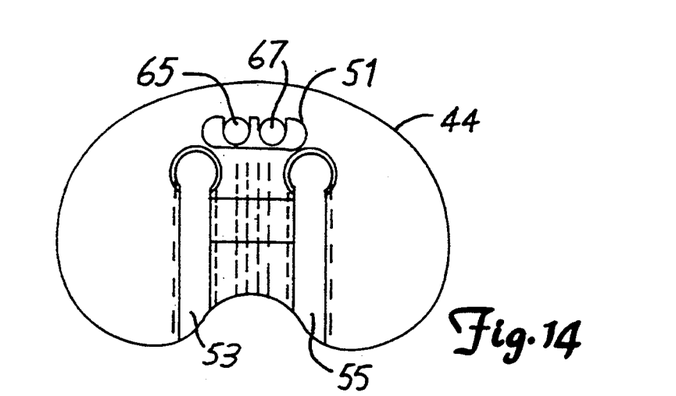
FIG. 14 is a bottom view of the tibial insert of FIG. 10.
Figure 15:
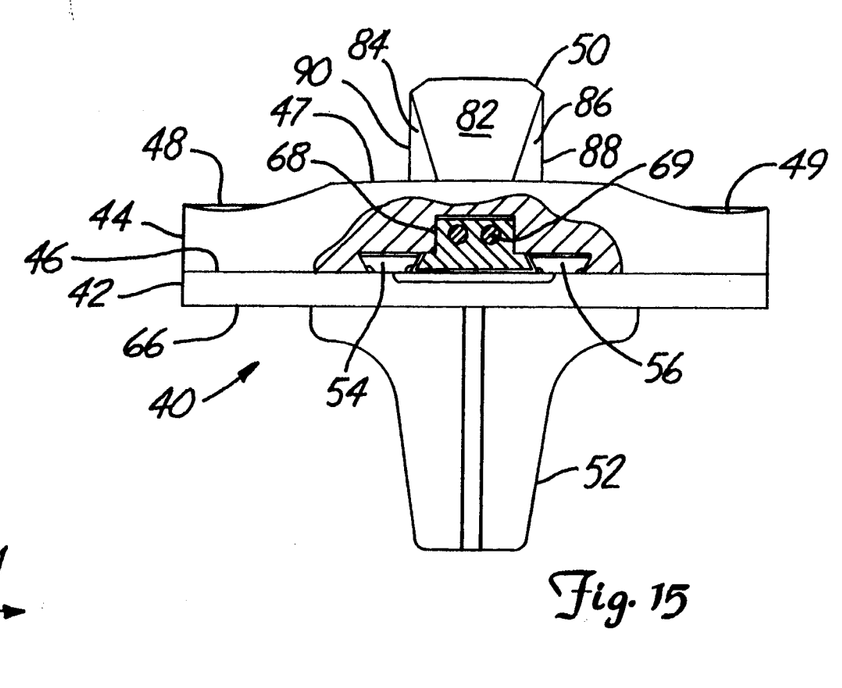
FIG. 15 is partially broken away anterior view of the tibial insert of FIG. 10.
Figure 16A:
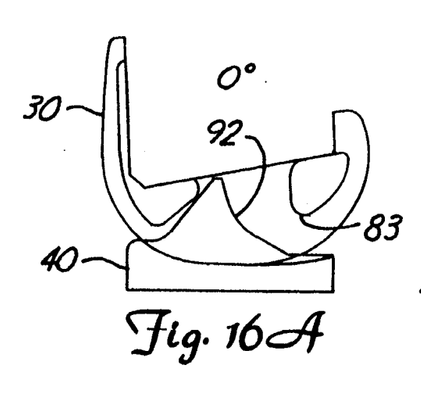
FIGS. 16A to 16F are schematic, cross sectional views showing particularly the contact between elements of the prosthesis as the leg is flexed through various angles.
Figure 16B:
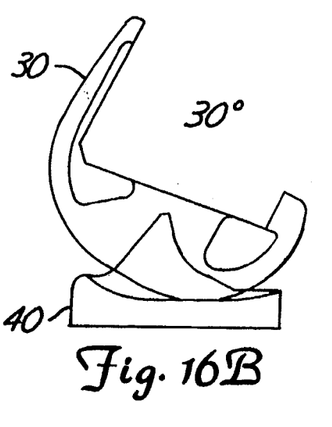
Figure 16C:
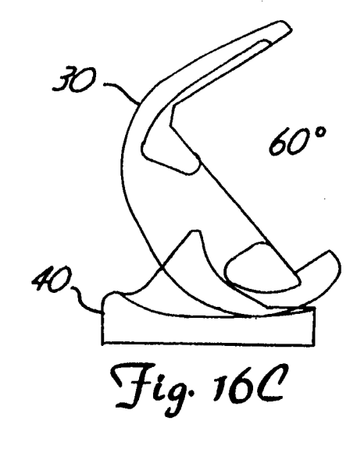
Figure 16D:
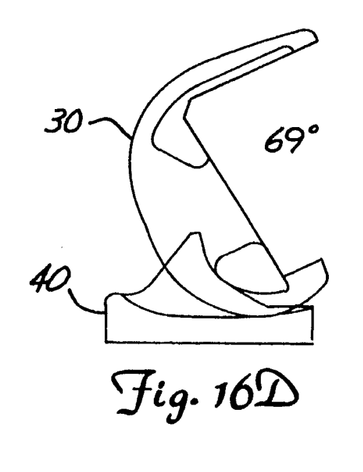
Figures 16E, 16F:
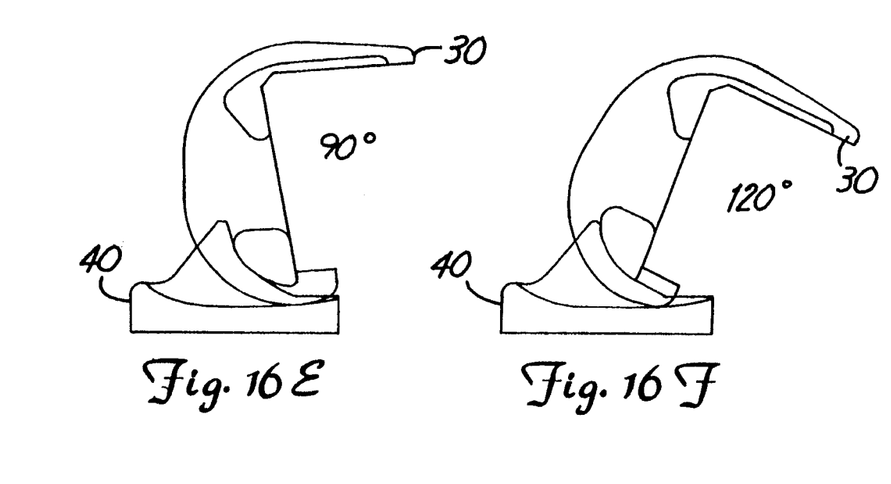

FIG. 14 shows the ends of a pair of metal studs 65, 67 which extend superiorly into the boss 51 a certain distance as shown in FIG. 13. These studs or pins reinforce the boss 51 to increase its resistance to backing out of the recess 57 in the tray 42.

In addition, in order to strengthen the dovetail attachment, a metal plug 68 is fitted in a recess between the grooves 53, 55 and held in place by metal pins 69 that extend through pin holes in the plastic insert 44 and the plug 68. The side walls of the plug 68 are cut to the dovetail angle and thus engage the dovetail bosses 54, 56.

This reinforcing arrangement increases the resistance to pull off of the insert 44. Although this reinforcement mechanism finds particular utility with the posterior stabilized knee tibial insert 44, it will be appreciated that it could be employed to reinforce any tibial insert should the need arise.

Alternatively, it will be appreciated that the reinforcement of the attachment of above-described tibial insert embodiment of the present invention could also be attained by other attachment mechanisms, including the CPD locking pin or bolt that could be inserted into a bore hole extending inferiorly through the eminence and matching bore hole extending inferiorly toward the stem of the tray, as is known in the art.

Any appropriate material known in the art may be used to make the component parts of the present inventive prosthesis. It is preferred that the tibial tray and stem portion and the femoral portion and its articulating surfaces be made of appropriate metal alloys, such as those containing cobalt, chromium, titanium and/or molybdenum known in the art and other appropriate non-corroding and non-toxic materials. The articulating surface of the tibial insert 46 is preferably made of low-friction plastics known in the art for this purpose, such as ultra-high molecular weight polyethylene, particular ASTMF 648-84.

Other modifications of the mechanical, implantable, modular knee prosthesis of the present invention may become readily apparent to those skilled in the art in light of the foregoing disclosure. Therefore, the scope of the present invention should be interpreted solely from the following claims, as such claims are written in light of the disclosure.

What is claimed is:

1. A knee joint prosthesis comprising:
   a femoral component adapted to be implanted on the condylar portion of the femur and having a pair of laterally spaced-apart condylar portions having smooth external surfaces that are convexly curved in the antero-posterior direction and generally match the shapes in lateral profile of the condylar surfaces of the femur and that are smoothly convexly curved in all cross sections along their antero-posterior extents, and an intercondylar portion interconnecting the condylar portions and defining an intercondylar recess having lateral side walls spaced-apart a predetermined distance, an anterior stop surface and a posterior camming member; and
   a tibial component adapted to be implanted on the tibial plateau and including a substantially flat platform portion having a superior surface bearing a pair of laterally spaced-apart concavities adapted to receive in nested relation the respective condylar portions of the femoral component, and an eminence extending superiorly from the platform portion and generally between the concavities, the eminence being adapted to be received in the intercondylar recess of the femoral component, the eminence having lateral surfaces, an anterior surface and a posterior surface, the relative positions and shapes of the anterior and posterior surfaces of the eminence and recess of the prosthesis as implanted in the knee joint being such as to permit relatively free antero-posterior translation of the components while restraining excessive anterior and posterior movements, and wherein the eminence includes lateral surfaces having portions essentially parallel to the lateral side walls of the recess defining a width of the eminence substantially narrower than the distance between the spaced-apart lateral side walls and portions angled with respect to anterior-posterior planes for enabling medial/lateral translation and substantial varus/valgus angulation and relative rotation between the tibial component and the femoral component throughout a substantial portion of the range of flexion.

2. A knee joint prosthesis comprising:
   a femoral component adapted to be implanted on the condylar portion of the femur and having a pair of laterally spaced-apart condylar portions, and an intercondylar portion interconnecting the condylar portions and defining an intercondylar recess having lateral side walls spaced-apart a predetermined distance, an anterior stop surface and a posterior camming member; and a tibial component comprising a tibial insert of plastic material fitted and held in a tibial tray adapted to be attached to the resected tibia, the tibial insert having a superior aspect comprising spaced-apart concavities and a tibial eminence therebetween and receivable in the intercondylar recess of the femoral component, and attachment means for attachment of the tibial insert to the tibial tray, the attachment means comprising a pair of dovetail-shaped bosses extending in parallel on the superior surface of the tibial tray and a recess extending perpendicularly to the bosses, and a like dimensioned pair of dovetail-shaped grooves formed in the inferior surface of the plastic tibial insert and a boss extending perpendicularly to the grooves, the boss on the insert having reinforcing metal inserts extending from the surface of the boss into the insert, the eminence being adapted to be received in the intercondylar recess of the femoral component, the eminence having lateral surfaces, an anterior surface and a posterior surface, the relative positions and shapes of the anterior and posterior surfaces of the eminence and recess of the prosthesis as implanted in the knee joint being such as to permit relatively free antero-posterior translation of the components while restraining excessive anterior and posterior movements, and wherein the eminence includes lateral surfaces having portions essentially parallel to the lateral side walls of the recess defining a width of the eminence substantially narrower than the distance between the spaced-apart lateral side walls and portions angled with respect to anterior-posterior planes for enabling medial/lateral translation and substantial varus/valgus angulation and relative rotation between the tibial component and the femoral component throughout a substantial portion of the range of flexion.

3. In a knee joint prosthesis of the type comprising:

a femoral component adapted to be implanted on the condylar portion of the femur and having a pair of laterally spaced-apart condylar portions having external surfaces that are smoothly convexly curved in the antero-posterior direction and generally match the shapes in lateral profile of the condylar surfaces of the femur and that are smoothly convexly curved in all cross sections along its antero-posterior extent; and a tibial component adapted to be implanted on the tibial plateau and including a substantially flat, non-metallic, tibial insert attached to a metal tibial tray, the insert having a superior surface bearing a pair of laterally spaced-apart concavities adapted to receive in nested relation the respective condylar portions of the femoral component, wherein the tibial insert is attached to the tibial tray by an attachment mechanism comprising interfitting dovetail-shaped bosses and grooves carried on mating surfaces of the tray and insert, respectively, the bosses containing imbedded metal reinforcing elements for making contact with the metal tibial tray and reinforcing the tibial insert from separating from the tibial tray.

4. The knee joint prosthesis of claim 3 wherein the attachment means of the tibial tray comprises a pair of dovetail-shaped bosses extending in parallel on the superior surface of the tibial tray and a recess extending perpendicularly to the bosses, and wherein the attachment means of the tibial insert comprises a like dimensioned pair of dovetail-shaped grooves formed in the inferior surface of the plastic tibial insert and a boss extending perpendicularly to the grooves, wherein the bosses on the insert is reinforced by metal inserts extending from the surface of the boss into the insert.

5. The knee joint prosthesis of claim 4 wherein the tibial insert further comprises metal reinforcing means inserted in the plastic for cooperative relationship with the dovetail-shaped bosses of the tibial tray when the dovetail-shaped grooves are fitted thereon.

6. A knee joint prosthesis comprising:

a femoral component adapted to be implanted on the condylar portion of the femur and having a pair of laterally spaced-apart condylar portions and an intercondylar portion interconnecting the condylar portions and defining an intercondylar recess having lateral side walls and a posterior bearing surface; and a tibial component adapted to be implanted on the tibial plateau and including a substantially flat platform portion having on its superior surface a pair of laterally spaced-apart concavities adapted to receive in nested relation the respective condylar portions of the femoral component, and an eminence extending superiorly from the platform portion and generally between the concavities for reception in the intercondylar recess of the femoral component, the eminence having lateral surfaces, an anterior surface and a posterior bearing surface, the relative positions and shapes of the anterior and posterior surfaces of the eminence and recess of the prosthesis as implanted in the knee joint being such as to permit relatively free relative antero-posterior translation of the components while restraining excessive anterior and posterior movements between the components, and wherein the respective posterior bearing surfaces of the tibial component and the femoral component are shaped so that as flexion of the knee increases, the force-transmitting contact area between such bearing surfaces increases.

7. The knee joint prosthesis of claim 6 wherein the tibial eminence includes lateral surfaces having portions that are essentially parallel to the lateral side walls of the recess and that define a width of the eminence substantially narrower than the distance between the spaced-apart lateral side walls of the intercondylar recess, the tibial eminence also having surface portions angled with respect to anterior-posterior planes for enabling medial/lateral translation and substantial varus/valgus angulation and relative rotation between the tibial component and the femoral component within a substantial portion of the range of flexion.

8. The knee joint prosthesis of claim 6 wherein said tibial component comprises a tibial insert of a plastic material fitted and held in a tibial tray adapted to be attached to the resected tibia, the tibial insert having a superior aspect comprising the spaced-apart concavities and the eminence therebetween and an inferior aspect having attachment means for attachment to the tibial tray, wherein the attachment means comprises metal reinforcing means fitted within the plastic material for making metal-to-metal attaching contact with the tibial tray.

9. The knee joint prosthesis of claim 8 wherein the attachment means comprises a pair of dovetail-shaped bosses extending in parallel on the superior surface of the tibial tray and a recess extending perpendicularly to the bosses, and wherein the tibial insert is provided with a like dimensioned pair of dovetail-shaped grooves formed in the inferior surface of the plastic tibial insert and a boss extending perpendicularly to the grooves, wherein the boss on the insert is reinforced by metal inserts extending from the surface of the boss into the insert.

10. The knee joint prosthesis of claim 9 wherein the tibial insert further comprises metal reinforcing means inserted in the plastic for cooperative relationship with the dovetail-shaped bosses of the tibial tray when the dovetail-shaped grooves are fitted thereon.

11. The knee joint prosthesis of claim 2 wherein the tibial insert further comprises metal reinforcing means inserted in the plastic for cooperative relationship with the dovetail-shaped bosses of the tibial tray when the dovetail-shaped grooves are fitted thereon.

12. A knee joint prosthesis comprising:
a femoral component adapted to be implanted on the condylar portion of the femur and having a pair of laterally spaced-apart condylar portions, and an intercondylar portion interconnecting the condylar portions and defining an intercondylar recess having lateral side walls spaced apart a predetermined distance, an anterior stop surface and a posterior camming member; and a tibial component comprising a tibial insert of plastic material fitted and held in a tibial tray adapted to be attached to the resected tibia, the tibial insert having a superior aspect comprising spaced-apart concavities for articulation with the condylar portions of the femoral component and a tibial eminence therebetween and receivable in the intercondylar recess of the femoral component, the eminence having lateral surfaces, an anterior surface and a posterior surface, the relative positions and shapes of the anterior and posterior surfaces of the eminence and recess of the prosthesis as implanted in the knee joint being such as to permit relatively free antero-posterior translation of the components while restraining excessive anterior and posterior movements, and wherein the eminence includes lateral surfaces having portions defining a width of the eminence substantially narrower than the distance between the spaced-apart lateral side walls and portions angled with respect to anterior-posterior planes for enabling medial/lateral translation and substantial varus/valgus angulation and relative rotation between the tibial component and the femoral component throughout a substantial portion of the range of flexion, the respective posterior bearing surfaces of the tibial component and the femoral component being so shaped that as flexion of the knee increases, the force-transmitting contact area between such bearing surfaces increases.

* * * * *